(12) United States Patent
Gage et al.

(10) Patent No.: US 11,504,461 B2
(45) Date of Patent: *Nov. 22, 2022

(54) ARTERIOVENOUS GRAFT FOR HEMODIALYSIS WITH PUNCTURE-RESISTANT POSTERIOR AND SIDE WALLS

(71) Applicant: W. L. Gore & Associates, Inc., Newark, DE (US)

(72) Inventors: Shawn M. Gage, Raleigh, NC (US); Jeffrey H. Lawson, Durham, NC (US)

(73) Assignee: W. L. Gore & Associates, Inc., Newark, DE (US)

( * ) Notice: Subject to any disclaimer, the term of this patent is extended or adjusted under 35 U.S.C. 154(b) by 509 days.

This patent is subject to a terminal disclaimer.

(21) Appl. No.: 16/580,423

(22) Filed: Sep. 24, 2019

(65) Prior Publication Data

US 2020/0016320 A1    Jan. 16, 2020

Related U.S. Application Data

(63) Continuation of application No. 15/450,523, filed on Mar. 6, 2017, now Pat. No. 10,420,874, which is a
(Continued)

(51) Int. Cl.
*A61M 1/36* (2006.01)
*A61M 39/02* (2006.01)

(52) U.S. Cl.
CPC ...... *A61M 1/3655* (2013.01); *A61M 39/0247* (2013.01); *A61M 2039/027* (2013.01);
(Continued)

(58) Field of Classification Search
CPC ............ A61M 1/3655; A61M 39/0247; A61M 2039/0258; A61M 2039/0264;
(Continued)

(56) References Cited

U.S. PATENT DOCUMENTS

| 4,619,641 A | 10/1986 | Schanzer |
| 5,192,310 A | 3/1993 | Herweck et al. |

(Continued)

FOREIGN PATENT DOCUMENTS

| EP | 1426067 | 6/2004 |
| WO | 2005/002661 | 1/2005 |

OTHER PUBLICATIONS

Office Action for corresponding Canadian Application No. 2,829,766 dated Jan. 10, 2018, 5 pages.
(Continued)

*Primary Examiner* — Philip R Wiest

(57) ABSTRACT

An arteriovenous dialysis access graft configured to be implanted in a subject includes: at least one flexible conduit having first and second end portions, wherein the first end portion is configured to connect to an artery of the subject and the second end portion is configured to connect to a vein of the subject such that blood flows through the at least one conduit; and at least one cannulation chamber positioned between the first end portion and the second end portion of the at least one conduit. The chamber includes: an elongated housing having an inlet and an outlet, a posterior wall, a pair of sidewalls, and an open anterior portion defining a cannulation port; and a self-sealing material extending across the cannulation port. The posterior wall and the sidewalls of the housing are formed of a substantially rigid material.

9 Claims, 18 Drawing Sheets

Related U.S. Application Data continuation of application No. 14/027,986, filed on Sep. 16, 2013, now Pat. No. 9,585,998, which is a continuation-in-part of application No. PCT/US2012/029449, filed on Mar. 16, 2012.

(60) Provisional application No. 61/453,211, filed on Mar. 16, 2011.

(52) U.S. Cl.
CPC ............... *A61M 2039/0258* (2013.01); *A61M 2039/0276* (2013.01)

(58) Field of Classification Search
CPC .... A61M 2039/027; A61M 2039/0276; A61M 2039/0282; A61M 2039/0288
See application file for complete search history.

(56) References Cited

U.S. PATENT DOCUMENTS

| | | | |
|---|---|---|---|
| 5,700,287 A | 12/1997 | Myers et al. | |
| 5,704,915 A | 1/1998 | Melsky et al. | |
| 5,713,859 A | 2/1998 | Finch, Jr. et al. | |
| 5,849,036 A | 12/1998 | Zarate | |
| 6,102,884 A | 8/2000 | Squitieri | |
| 6,146,414 A | 11/2000 | Gelman | |
| 6,261,257 B1 | 7/2001 | Uflacker et al. | |
| 7,108,673 B1 | 9/2006 | Batiste | |
| 7,261,705 B2 * | 8/2007 | Edoga | A61M 1/3653 604/6.16 |
| 7,452,374 B2 | 11/2008 | Hain et al. | |
| 7,566,317 B1 | 7/2009 | Batiste et al. | |
| 7,762,977 B2 | 7/2010 | Porter et al. | |
| 7,780,622 B2 | 8/2010 | Fitzpatrick | |
| 7,806,922 B2 | 10/2010 | Henderson et al. | |
| 7,828,781 B2 * | 11/2010 | Edoga | A61M 39/0208 604/288.03 |
| 7,833,186 B1 | 11/2010 | Batiste | |
| 8,029,563 B2 | 10/2011 | House et al. | |
| 8,066,758 B2 | 11/2011 | Bogert et al. | |
| 8,906,087 B2 | 12/2014 | House et al. | |
| 9,585,998 B2 * | 3/2017 | Gage | A61M 1/3655 |
| 10,420,874 B2 * | 9/2019 | Gage | A61M 39/0247 |
| 2003/0100859 A1 | 5/2003 | Henderson et al. | |
| 2004/0193106 A1 | 9/2004 | Miller | |
| 2006/0118236 A1 | 6/2006 | House et al. | |
| 2007/0123811 A1 | 5/2007 | Squitieri | |
| 2009/0209921 A1 | 8/2009 | Claude et al. | |
| 2011/0060264 A1 | 3/2011 | Porter et al. | |

OTHER PUBLICATIONS

International Search Report and Written Opinion for PCT/US2012/029449 dated Oct. 29, 2012.
Gage et al., "New Developments in Hemodialysis Grafts", Endovascular Today, Jun. 2010, pp. 38-44.
European Search Report corresponding to European application No. 12757046.3, dated Jan. 3, 2014, 7 pages.
International Preliminary Reporton Patentability for PCT/US2012,029449 dated Sep. 26, 2013, 6 pages.

\* cited by examiner

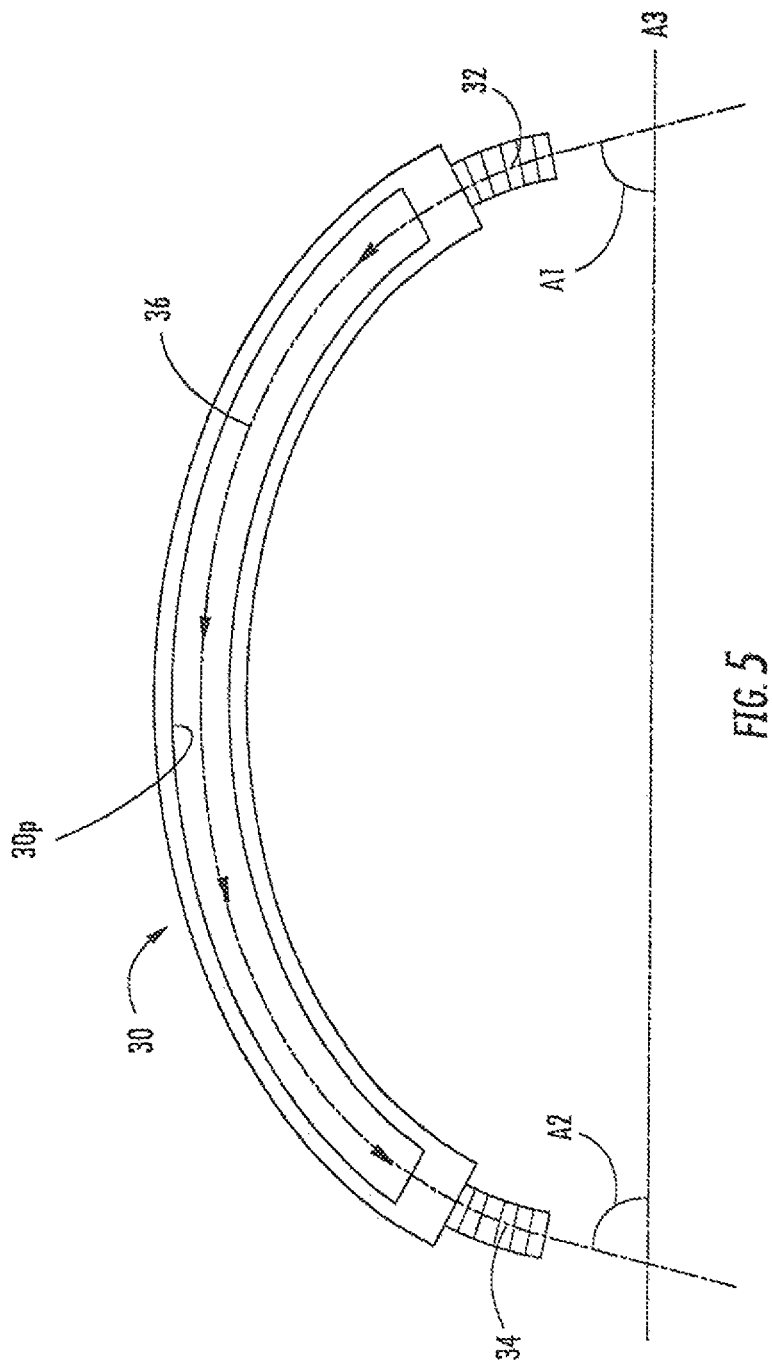

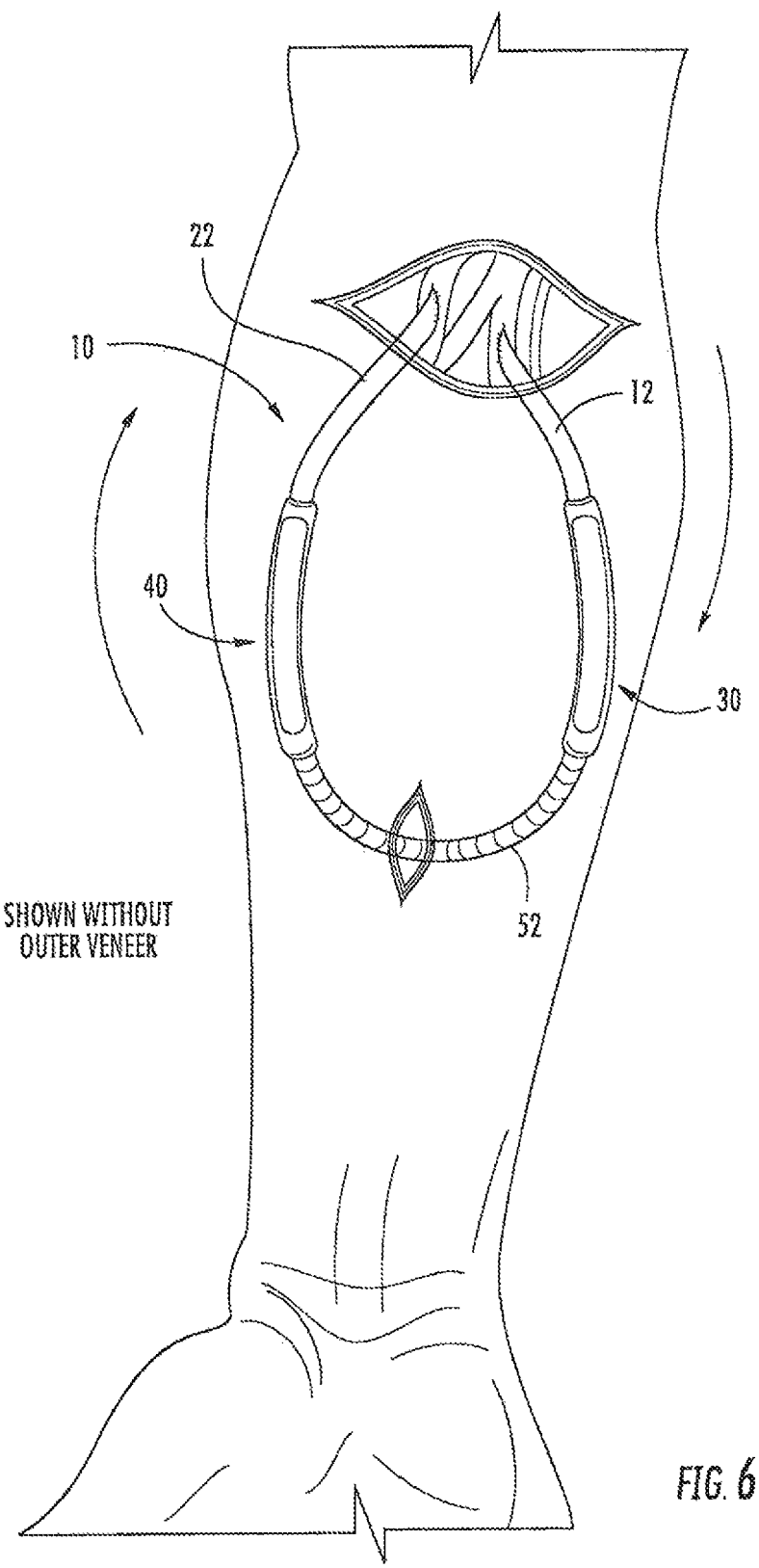

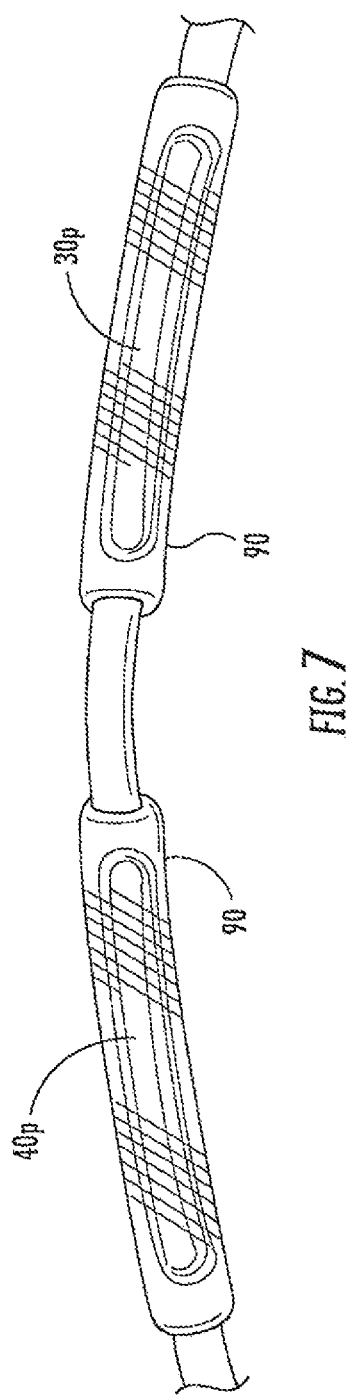

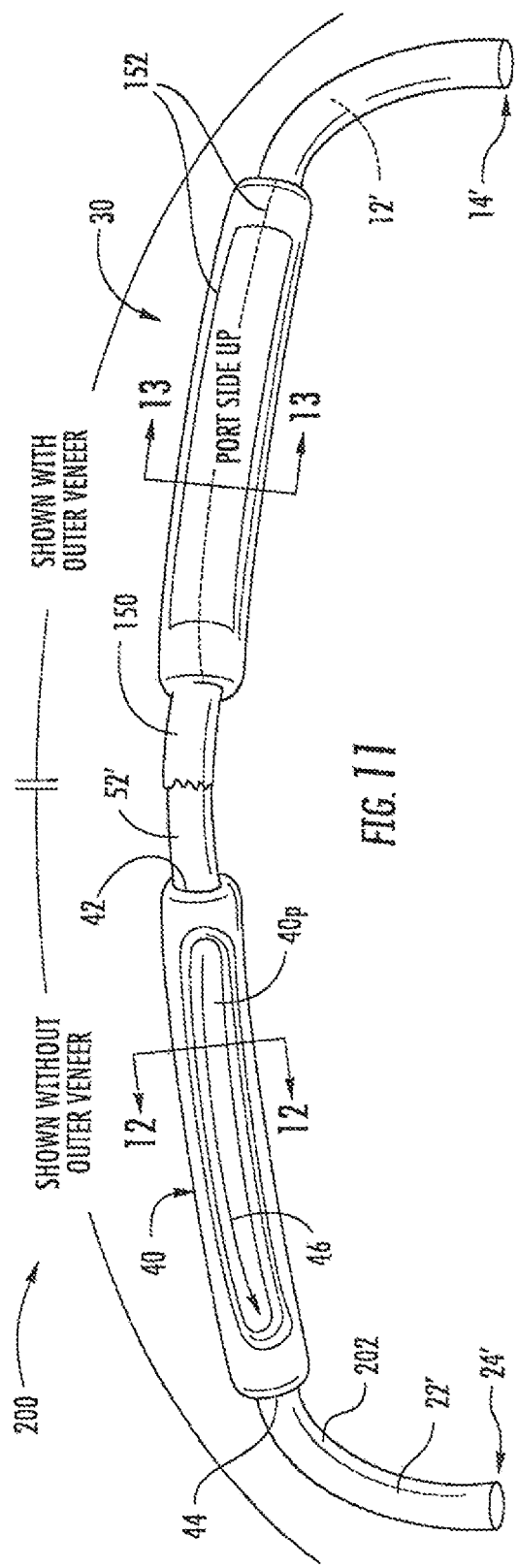
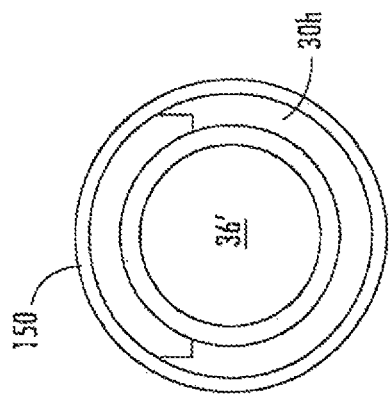
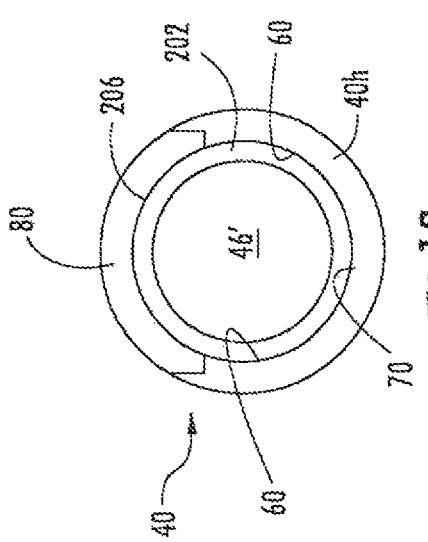

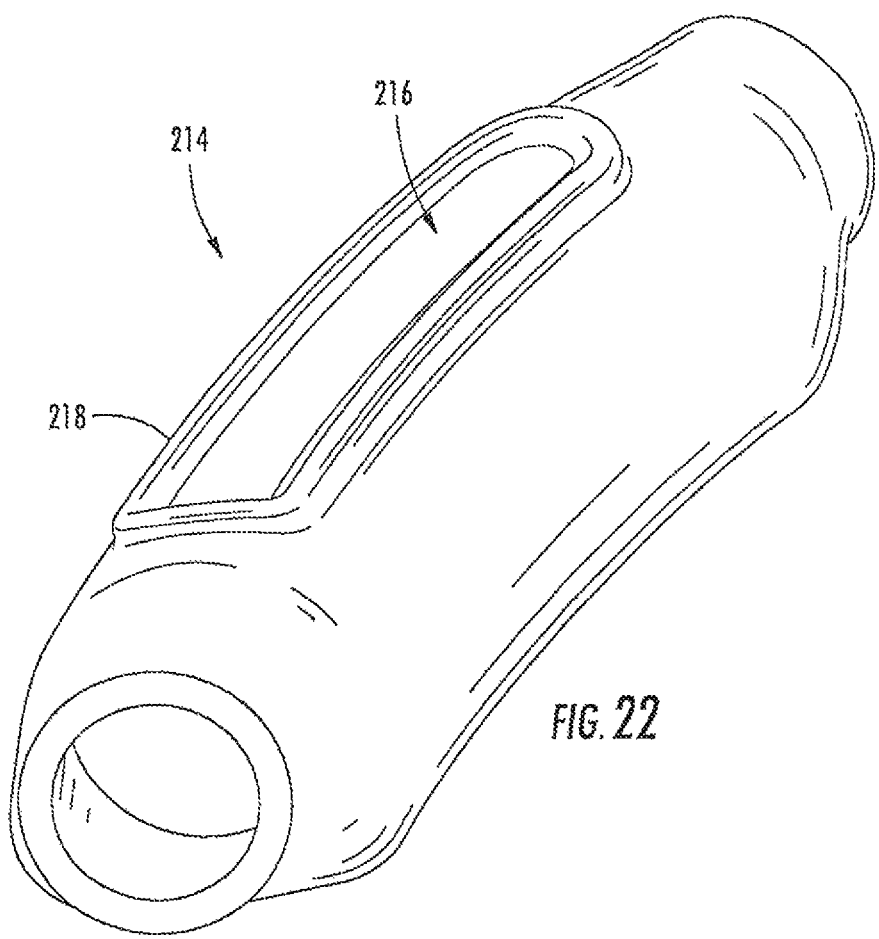

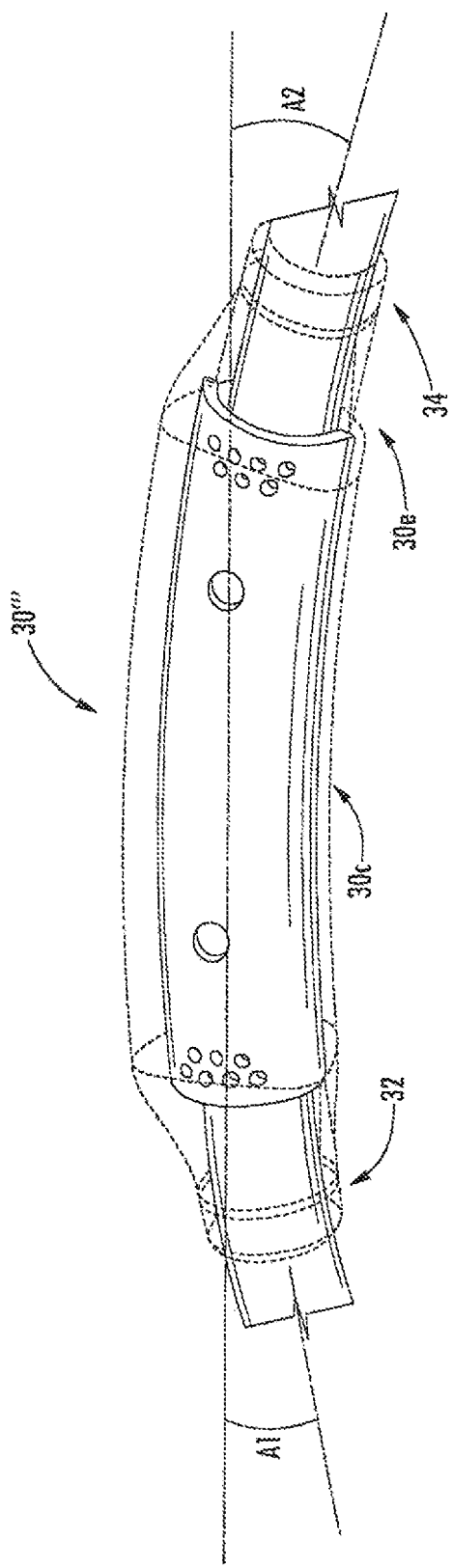

ARTERIOVENOUS GRAFT FOR HEMODIALYSIS WITH PUNCTURE-RESISTANT POSTERIOR AND SIDE WALLS

RELATED APPLICATIONS

This application is a continuation of U.S. patent application Ser. No. 15/450,523, filed Mar. 6, 2017, which is a continuation of U.S. patent application Ser. No. 14/027,986, filed Sep. 16, 2013, which is a continuation-in-part of International Application No. PCT/US2012/029449, filed Mar. 16, 2012, which claims priority to U.S. Provisional Patent Application No. 61/453,211, filed Mar. 16, 2011, the disclosures of which are incorporated by reference herein in their entireties.

FIELD OF THE INVENTION

This invention relates to grafts and, more particularly, to arteriovenous grafts for dialysis.

BACKGROUND

Dialysis treatment of individuals suffering from renal failure requires that blood be withdrawn and cycled through a dialysis machine that performs the function of the failed kidneys. This process, termed hemodialysis, must be repeated at a regular interval (e.g., three times per week) and thus requires repeated punctures using dialysis needles. Relatively large gauge needles are required to promote the high flow rates required during dialysis. Frequent puncturing of autogenous arteriovenous access as well as prosthetic arteriovenous access with large bore needles can cause trauma, conduit degeneration, hematoma formation, pseudoaneurysm formation, loss of patency, or even hemorrhage and exsanguination.

A common technique to provide vascular access for hemodialysis, therefore, is to connect a prosthetic graft or shunt between an artery and a vein in, for example, the upper or lower extremity. Occasionally, patient complexity may also warrant access placement on the chest or abdominal wall. Conventional arteriovenous grafts (AVGs) are often constructed of a polymeric material such as expanded polytetrafluoroethylene (ePTFE) or polyetherurethaneurea.

A significant mode of failure of AVGs is related to a traumatic cannulation with the dialysis needle. This may occur as the needle traverses the anterior wall of the AVG and then continues through the posterior wall (or a sidewall) of the graft. This type of trauma causes a defect in the posterior and/or side wall of the graft and often results in hematoma formation which can ultimately lead to graft thrombosis (i.e., the formation of a blood clot inside the graft, obstructing the flow of blood therethrough) by external compression of the graft and ultimate graft failure.

Moreover, repeated punctures of the graft material (such as ePTFE) promotes coring and degeneration of the graft material which often leads to rupture of the graft, pseudoaneurysm formation, and graft thrombosis. Also, ePTFE grafts are generally not self-sealing when punctured and usually require implantation three, four or more weeks prior to puncture to allow for graft incorporation (a layer of fibrotic tissue that attaches to the outside surface of the graft). The layer of fibrotic tissue may prevent leakage of blood through the wall of the graft upon withdrawal of the dialysis needles and if cannulated before this time could lead to hematoma formation between the graft and surrounding tissue. This hematoma could cause adverse events such as graft occlusion, lack of incorporation of the graft and increased chance for infection. However, there is often very little subcutaneous tissue between the surface of the skin and the anterior face of the graft, and the above-mentioned problems may occur even after waiting for tissue incorporation.

U.S. Pat. No. 6,146,414 to Gelman, the disclosure of which is incorporated herein in its entirety, describes tube grafts having expanded regions and shields at posterior portions of the expanded regions. The shields have added rigidity relative to the tube to thereby signal to the operator when the needle tip hits a shield during cannulation. The shields are either incorporated into the tube graft or are added as a separate component during assembly, thereby adding complexity to the manufacturing process. The Gelman patent describes that the shields may be rigid or semi-rigid but only describes straight grafts (i.e., grafts without curvature). Substantially rigid shields would require that the grafts described in the Gelman patent be kept in a generally straight configuration, and such a configuration may be difficult or impossible to use at many AVG implantation sites, such as forearms and upper arms. Semi-rigid shields may allow for some bending of the graft to accommodate placement in these areas, but would reduce or eliminate the capability of the shield to prevent needle penetration through the shield or warn the operator of impending penetration. Also, bending of grafts employing semi-rigid shields could weaken the graft and/or disrupt flow characteristics for blood flowing therethrough. Finally, the Geman patent does not recognize the need for a self-sealing graft or a portion thereof.

Self-sealing vascular access grafts have been described in, for example, U.S. Pat. No. 5,192,310 to Herweck et al., U.S. Pat. No. 7,452,374 to Hain et al., and U.S. Pat. No. 7,780,622 to Fitzpatrick et al., the disclosures of which are incorporated herein in their entireties. However, none of these patents consider the problem of dialysis needles puncturing side walls or anterior walls during cannulation. U.S. Pat. No. 6,261,257 to Uflacker et al., the disclosure of which is incorporated herein in its entirety, describes grafts with straight port chambers including self-sealing septums. The problem of puncturing side walls or anterior walls during cannulation is also not contemplated in the Uflacker patent. Even if the straight chambers were constructed of a rigid material to ostensibly provide puncture resistance, such a configuration would not be suitable for implantation in the upper or lower extremities, as described above.

Thus, there is a need for arteriovenous grafts configured to be implanted in a subject (e.g., in an upper or lower extremity of a subject) with puncture resistant posterior walls and side walls. There is also a need for such arteriovenous grafts to include self-sealing ports at the anterior surfaces of the graft. Such designs may help prevent traumatic cannulations and/or graft degeneration so as to lead to higher patency rates for arteriovenous grafts, decrease the risk of hemorrhage or infection for hemodialysis patients, and reduce overall vascular access related healthcare costs.

SUMMARY

Embodiments of the invention are directed to an arteriovenous dialysis access graft configured to be implanted in a subject. The arteriovenous graft (AVG) includes at least one flexible conduit having first and second end portions, wherein the first end portion is configured to connect to an artery of the subject and the second end portion is configured to connect to a vein of the subject such that blood flows through the at least one conduit from the first end portion to the second end portion. The AVG includes at least one cannulation chamber positioned between the first end portion and the second end portion of the at least one conduit. The at least one chamber includes: an elongated housing having an inlet at a first end thereof and an outlet at a second, opposed end thereof, a posterior wall, a pair of sidewalls, and an open anterior portion defining a cannulation port; a self-sealing material extending across the cannulation port; and a longitudinal passageway defined by the housing and the self-sealing material that extends from the inlet to the outlet of the housing. The housing of the at least one chamber is formed of a substantially rigid material such that, when a dialysis needle is inserted through the self-sealing material and the cannulation port, the needle is inhibited or prevented from extending through the posterior or the side walls of the housing.

According to some embodiments, the at least one chamber comprises a plurality of chambers. According to some embodiments, the at least one conduit extends through the longitudinal passageway of the chamber(s).

According to other embodiments, the at least one conduit comprises first and second flexible conduits. Each conduit has a first and second end. The first end of the first conduit is configured to connect to the artery of the subject and the second end of the first conduit is connected to the inlet of the chamber; the first end of the second conduit is configured to connect to the vein of the subject and the second end of the second conduit is connected to the outlet of the of the chamber.

According to some embodiments, the at least one cannulation chamber comprises first and second cannulation chambers and the at least one conduit comprises first, second and third flexible conduits, with each conduit having a first and second end. The first end of the first conduit is configured to connect to the artery of the subject and the second end of the first conduit is connected to the inlet of the first chamber; the first end of the second conduit is configured to connect to the vein of the subject and the second end of the second conduit is connected to the outlet of the of the second chamber; and the first end of the third conduit is connected to the outlet of the first chamber and the second end of the third conduit is connected to the inlet of the second chamber.

According to some embodiments, at least one of the first and second chambers is curved such that the longitudinal passageway has an are angle. The arc angle may be between about 5 and about 45 degrees to accommodate placement in an upper arm of the subject. The are angle may be between about 5 degrees and about 60 degrees to accommodate placement in a forearm or lower extremity of the subject.

The self-sealing material may be formed of a stretchable material such as silicone or polyurethane. The conduit(s) may be formed of a biocompatible polymeric material such as ePTFE. The chamber housing(s) may be formed of a biocompatible material such as titanium or a rigid polymer. Each chamber housing material may provide tactile and/or audible feedback to an operator that the dialysis needle has contacted an interior portion of the posterior wall or one of the side walls.

BRIEF DESCRIPTION OF FIGURES

FIG. 5 is a top view of a curved cannulation chamber for use with the AVG of FIG. 1 according to some embodiments.
FIG. 6 is a schematic illustration of the AVG of FIG. 1 implanted in an upper extremity (forearm) of a subject according to some embodiments.
FIG. 7 is a top view of the AVG of FIG. 1 with a member comprising self-sealing material extending across the each of the cannulation chambers according to some embodiments.
FIG. 11 is a schematic illustration of an AVG according to some other embodiments.
FIGS. 12 and 13 illustrate cross-sectional views of cannulation chambers of the AVG of FIG. 11 according to some embodiments.
FIG. 22 is a perspective view of an outer layer of the cannulation chamber of FIG. 19 according to some embodiments.
FIG. 23 is a bottom view of a curved cannulation chamber for use with the AVG of FIG. 18 according to some embodiments.

DETAILED DESCRIPTION

Figure 1:
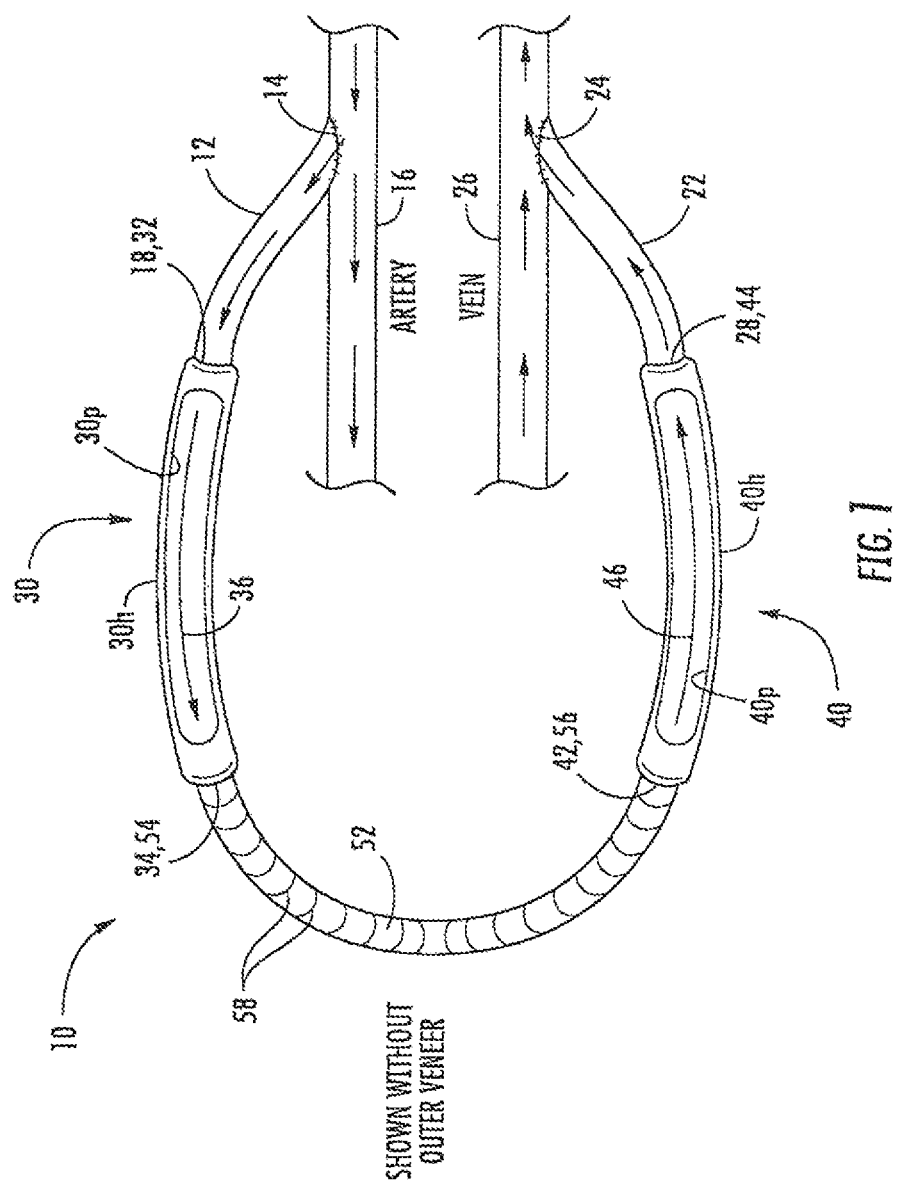
FIG. 1 is a schematic illustration of an arteriovenous graft (AVG) according to some embodiments.

The present invention now will be described more fully with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

As used herein, the terms "comprising" or "comprises," "having" or "has," and "including" or "includes" are open-ended, and includes one or more stated features, integers, elements, steps, components or functions but does not preclude the presence or addition of one or more other features, integers, elements, steps, components, functions or groups thereof. As used herein, the term "and/or" includes any and all combinations of one or more of the associated listed items.

As used herein, the common abbreviation "e.g.," which derives from the Latin phrase "exempli gratia," may be used to introduce or specify a general example or examples of a previously mentioned item, and is not intended to be limiting of such item. If used herein, the common abbreviation "i.e.," which derives from the Latin phrase "id est," may be used to specify a particular item from a more general recitation.

The terminology used herein is for the purpose of describing particular embodiments only and is not intended to be limiting of the invention. As used herein, the singular forms "a," "an" and "the" are intended to include the plural forms as well, unless the context clearly indicates otherwise.

Well-known functions or constructions may not be described in detail for brevity and/or clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In addition, spatially relative terms, such as "under," "below," "lower," "over," "upper," "downward," "upward," "inward, "outward" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Turning now to the figures, an arteriovenous graft (AVG) 10 according to some embodiments is illustrated in FIGS. 1-4. The AVG 10 is configured to be implanted in a subject. The AVG 10 includes a first flexible conduit 12 having a first end 14 configured to be connected to an artery 16 of the subject and a second end 18. The AVG 10 also includes a second flexible conduit 22 having a first end 24 configured to be connected to a vein 26 of the subject and a second end 28. In this regard, blood flows from the first end 14 of the first conduit 12 to the first end 24 of the second conduit 22. It is noted that the graft 10 could be used as an arterial-arterial graft (for example, vein 26 could instead be an artery).

A first cannulation chamber 30 has a housing 30h including an inlet 32 connected to the second end 18 of the first conduit 12 and an outlet 34. The chamber housing 30h has an open anterior portion including an aperture defining a cannulation port 30p. The cannulation port 30p is configured to receive a dialysis needle N (FIGS. 3 and 4) therethrough.

Similarly, a second cannulation chamber 40 has a housing 40h including an inlet 42 and an outlet 44 connected to the second end 28 of the second conduit 22. The chamber housing 40h also has an open anterior portion including an aperture defining a cannulation port 40p. The cannulation port 40p is configured to receive a dialysis needle N (FIGS. 3 and 4) therethrough.

A third flexible conduit 52 connects the first chamber 30 and the second chamber 40. As illustrated, the third conduit 52 includes a first end 54 connected to the outlet 34 of the first chamber housing 30h and a second end 56 connected to the inlet 42 of the second chamber housing 40h.

The conduits 12, 22, 52 may be formed of an inert biocompatible material such as ePTFE, polyurethane, Dacron, or the like. The conduits may also be formed of other biological materials, such as animal or human vessels, or biologically engineered tissue conduit.

One or more of the conduits 12, 22, 52 may be non-kinking or kink-resistant. For example, one or more of the conduits may be corrugated and/or include beading material on at least a portion of its outer periphery. As illustrated in FIG. 1, beading material 58 is included on the outer periphery of the third conduit 52. Such beading material may be in the form of ePTFE wrapped around the outer surface in a spiral or helical configuration, for example. In some embodiments, the third conduit 52 is non-kinking (or more kink-resistant than one or both of the other conduits 12, 22) to account for possible increased bending at this portion of the graft.

Figure 3:
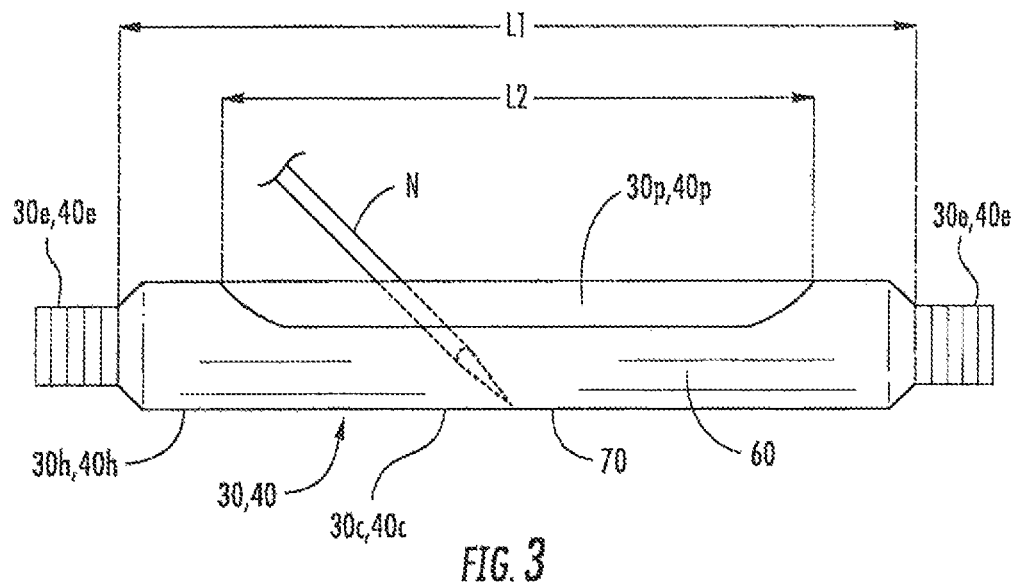
FIG. 3 is a side view of a cannulation chamber of the AVG of FIG. 1 according to some embodiments.
Figure 4:
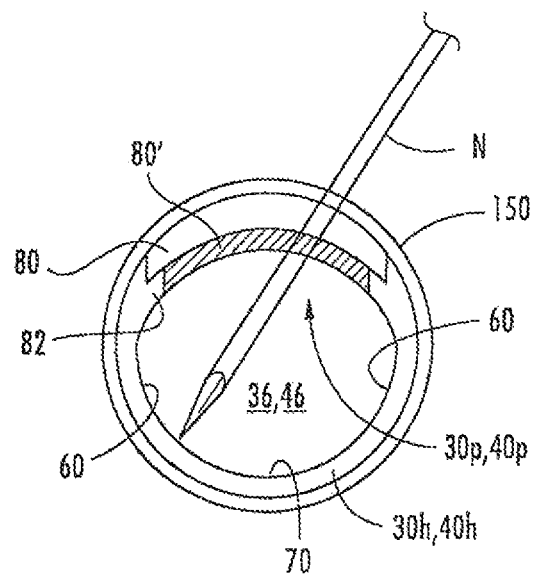
FIG. 4 is a cross-section view of a cannulation chamber of the AVG of FIG. 1 according to some embodiments.

Referring to FIGS. 3 and 4, each chamber housing 30h, 40h includes a pair of opposed sidewalls 60 and a posterior wall 70. As illustrated, the sidewalls 60 extend downwardly from the cannulation port 30p to the posterior wall 70.

In some embodiments, the first and second chamber housing 30h, 40h are formed of a substantially rigid biocompatible material (e.g., titanium or a substantially rigid polymer or composite) such that, when a dialysis needle is inserted through the cannulation port 30p, 40p of a respective chamber, the needle is prevented or substantially prevented from extending through the posterior wall 70 or one of the side walls 60 of the chamber housing. In some other embodiments, the first and second chamber housings 30h, 40h are formed of a semi-rigid biocompatible material (e.g., a puncture-resistant composite) such that, when a dialysis needle is inserted through the cannulation port 30p, 40p of a respective chamber, the needle is inhibited from extending through the posterior wall 70 or one of the side walls 60 of the chamber housing. In either case, the chamber housing material may provide tactile and/or audible feedback to an operator that the dialysis needle has contacted an interior portion of the posterior wall or one of the side walls.

A self-sealing material (e.g., but not limited to, silicone) may extend across, lie beneath and/or extend over the apertures defining the cannulation ports 30p, 40p. In the embodiment shown in FIG. 2, the self-sealing material 80 extends across the open anterior portion of the housings 30h, 40h. In some embodiments, the self-sealing material 80 is adhered to the housings 30h, 40h via a medial-grade adhesive (not shown). Enclosed longitudinal passageways 36, 46 (FIG. 1) are defined by the housings 30h, 40h and the self-sealing material 80. The longitudinal passageways extend from the inlet to the outlet of the chamber housing. For example, referring to the chamber 30, the longitudinal passageway 36 extends from the inlet 32 to the outlet 36 of the chamber housing 30h. In the illustrated embodiment, the longitudinal passageways 36, 46 define longitudinal fluid flow paths or ports wherein blood may flow therethrough. It will be appreciated from the discussion below that, in other embodiments, conduits may extend through the longitudinal passageways 36, 46.

The chamber housings 30h, 40h and/or the self-sealing material 80 may be shaped and configured such that the longitudinal passageways 36, 46 have a circular or substantially circular cross-section. In those embodiments in which fluid flows through the passageways 36, 46, this configuration can minimize disturbance of laminar flow therethrough. Similarly, in those embodiments in which the conduits extend through the passageways 36, 46, this configuration can allow the conduits to retain their circular or substantially circular cross-section or shape to inhibit flow disturbances therethrough.

The self-sealing material 80 is made of a stretchable material that is suitable for repeated punctures. The needle N (FIGS. 3 and 4) is inserted through the cannulation ports 30p, 40p and the self-sealing material 80. The self-sealing material 80 is then able to self-seal after removal of the needle N. The needle N may have a beveled end so as to create more of a "slit-like" puncture in the self-sealing material 80, which may be easier to "heal" or seal. In various embodiments the self-sealing material 80 may have a thickness of between about 1 mm and about 10 mm and between about 1 mm and about 5 mm.

The cannulation ports 30p, 40p may have a length that spans a major portion of the length of the chamber housings 30h, 40h. This provides an increased area through which a clinician can make the repeated cannulations needed during hemodyalisis (i.e., it permits the clinician to "rotate" the needle puncture site more effectively and with less trauma to the self-sealing ports and the graft in general). Referring to FIG. 3, in various embodiments, the chamber housings 30h, 40h may have a length L1 of between about 8 cm and about 20 cm and between about 10 cm and about 15 cm. In some embodiments, the length L1 of the chamber housings is about 10 cm or about 12 cm. The length L1 may be inclusive of end portions 30e, 40e, which are described in more detail below. In various embodiments, the cannulation ports 30p, 40p may have a length L2 of between about 6 cm and about 18 cm, between about 8 cm and about 13 cm and between about 6 cm and about 10 cm.

Figure 2:
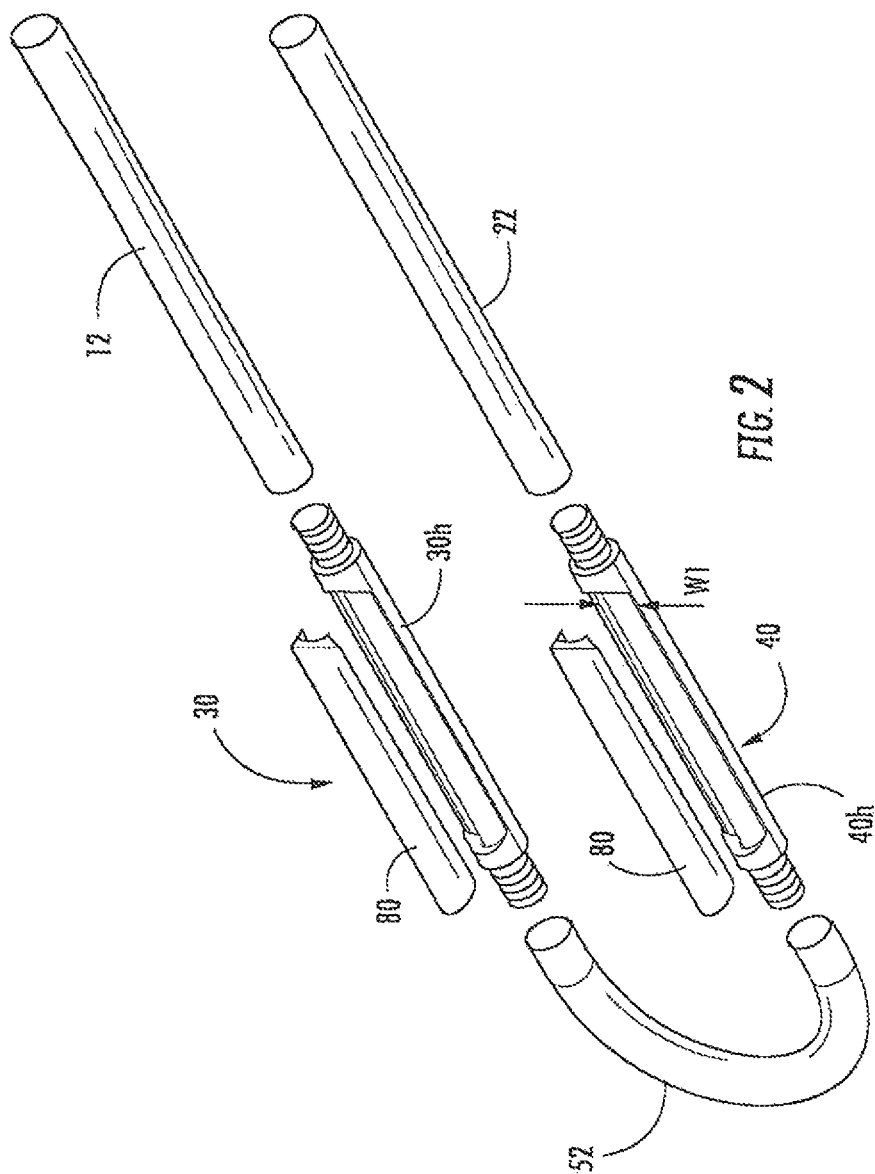
FIG. 2 is an exploded view of the AVG of FIG. 1 according to some embodiments.

Furthermore, the cannulation ports 30p, 40p may have a width transverse to the length L2 that is chosen to be large enough to facilitate cannulation (i.e., targeting of the needle). The ports 30p, 40p may also have a width that is chosen such that the ports (or, put another way, the apertures on the anterior face/surface of the chamber housings) do not extend too far along the perimeter of the chamber housings 30h, 40h. Referring to FIG. 2, in various embodiments, the ports 30p, 40p have a width W1 of between about 6 mm and about 12 mm and about 8 mm and about 10 mm.

As shown in FIGS. 2 and 3, the chamber housings 30h, 40h may include a substantially cylindrical center portion 30c, 40c and opposed end portions 30e, 40e (the chambers 30, 40 may be thought of as being "torpedo-shaped"). This configuration may aid in tunneling through subcutaneous tissue when the graft is being implanted. The end portions 30e, 40e may be sized and configured to receive the conduits 12, 22, 52. As illustrated, the end portions 30e, 40e have a barbed outer surface (i.e., an outer surface with a plurality of raised outer portions). The ends of the conduits 12, 22, 52 may snugly fit over the end portions 30e, 40e of the chamber housings.

Still referring to FIGS. 2 and 3, the chamber housings 30h, 40h have a reduced outer diameter and/or thickness at their end sections 30e, 40e. The inner diameter of the end portions 30e, 40e and the center 30c, 40c of the chambers 30, 40 may be equal or substantially equal so as to minimize flow disturbance therethrough.

In some embodiments, the center portions of the chambers 30c, 40c can have an inner diameter between about 4 mm and about 10 mm and, in some embodiments, between about 6 mm and about 8 mm. The center portions 30c, 40c can have an outer diameter of between about 7 mm and about 13 mm and, in some embodiments, between about 10 mm and about 12 mm. The center portions 30c, 40c can have a wall thickness of between about 1 mm and about 3 mm. The end portions of the chambers 30e, 40e may have an inner diameter between about 4 mm and about 8 mm and, in some embodiments, between about 5 mm and about 8 mm. The end portions 30e, 40e can have an outer diameter of between about 5 mm and about 10 mm and, in some embodiments, between about 6 mm and about 10 mm. The flexible conduits 12, 22, 52 may have an inner diameter between about 4 mm and about 8 mm and between about 6 mm and about 8 mm in various embodiments. The flexible conduits 12, 22, 52 may have an outer diameter of between about 7 mm and about 9 mm.

In some embodiments, the inner diameter of the end portions 30e, 40e and the center portions 30c, 40c are equal or substantially equal to promote laminar fluid flow. The center portions 30c, 40c may have a larger outer diameter than the end portions 30e, 40e (for example, the center portions may have an outer diameter of about 10 mm and the end portions may have an outer diameter of about 8 mm to accommodate 8 mm inner diameter conduit or tubing). As such, in these embodiments, the center portions 30c, 40c have a greater material thickness than the end portions 30e, 40e. It is noted that the increased relative thickness of the material at the center portion 30c, 40c may provide added puncture resistance during cannulation.

The chamber housings 30h, 40h may generally have a stepped configuration with shoulders separating the end portions 30e, 40e and the center portion 30c, 40c (FIG. 2) or at least a portion of the center portion 30c, 40c and/or the end portions 30e, 40e may be tapered (FIG. 3).

It is noted that connectors may be employed to connect the conduits 12, 22, 52 and the inlets/outlets of the chamber housings 30h, 40h. For example, the end portions 30e, 40e may be excluded. The chambers housings 30h, 40h and/or the conduits 12, 22, 52 may include a connector or be sized and configured to fit together (e.g., press-fit). The chambers and conduits may be connected in such a way so as to minimize any relative difference in flow area and shape (e.g., maintain a consistent flow path through the graft).

In some embodiments, the graft 10 may have a total (extended) length of between about 30 cm and about 80 cm. The conduits 12, 22, 52 may each have a length of between about 5 cm and about 15 cm. The ends of the conduits 12, 22 may be trimmed and/or shaped in order to fashion an anastomosis. The ends of the conduits 12, 22 may also have a hooded configuration to present additional options for anastomosis creation.

In some embodiments, the graft is versatile so as to be implanted in different or particular configurations in the body of a subject depending on the implantation location chosen based on suitable vascular anatomy. In this regard, the chambers 30, 40 (or chamber housings 30h, 40h) may be curved to a varying degree to suit implantation in various locations throughout the body. As described above, the chamber housings 30h, 40h may be formed of a material that has a certain rigidity so as to be puncture-resistant or puncture-proof with respect to a cannulating dialysis needle during a typical hemodialysis procedure. This rigidity may not allow for the clinician to adequately bend the chambers during implantation in certain locations of the body (e.g., the upper and lower arm). As a result, puncture-resistant chambers/housings that are substantially straight or are not curved to the proper degree may not be used in certain applications. Further, chambers that are not properly curved for a particular application may result in increased bending or kinking of the conduits 12, 22, 52 and which may impart added stress on the conduits and/or produce a more restrictive or tortuous flow path.

Thus, referring to FIG. 5, the cannulation chambers may be provided as curved to varying degrees. The chamber 30 is shown with the longitudinal passageway 36 extending from the inlet 32 to the outlet 34. A curve angle A1 (also referred to herein as an arc angle A1) is defined by the angle between the passageway 36 at or extending from the inlet 32 and the axis A3. The axis A3 is parallel to a longitudinal axis that would be defined by a "straight" chamber. Similarly, a curve angle A2 (also referred to herein as an arc angle A2) is defined by the angle between the passageway 36 at or extending from the outlet 34 and the axis A3. The chamber 30 may generally be symmetrical; that is, the angles A1 and A2 may be equal. For the purposes of the present application, a chamber/housing generally referred to as having an "arc angle" or a "curve angle" or being "curved" to a certain value (e.g., number of degrees) is a chamber/housing that has equal or substantially equal angles A1 and A2.

The chambers may be curved from between about 0 degrees and about 60 degrees. In other words, each of the arc or curve angles A1 and A2 may be between about 0 degrees and about 60 degrees. The curved chamber creates a curved longitudinal passageway or flow path therethrough. In some embodiments, the chambers are gently and/or evenly curved. As illustrated, the curved chambers may be configured such that surface area of the cannulation port 30p on the anterior face/surface of the housing retains its advantageously large "target" cannulation area.

In various embodiments, the chambers are curved between about 10 and about 45 degrees, between about 15 and about 45 degrees, between about 10 and about 40 degrees, and between about 10 and about 30 degrees so as to be configured to be implanted in the arm of a subject. The two chambers 30, 40 may have the same or differing curvature in various embodiments.

In some embodiments, one or both chambers are curved between about 0 and about 45 degrees, between about 5 and about 45 degrees, between about 0 and about 25 degrees, between about 5 and about 20 degrees, between about 10 and 20 degrees, and between about 5 and 15 degrees so as to be configured to be implanted in an upper arm of a subject (e.g., form part of an upper arm loop graft). In various embodiments, one or both chambers are curved between about 5 and about 60 degrees, between about 10 and about 50 degrees, between about 20 and about 45 degrees, between about 20 and 40 degrees, and between about 25 and 35 degrees so as to be configured to be implanted in a forearm of a subject (e.g., form part of a forearm loop graft) or in a lower extremity of a subject.

In various embodiments, one or both chambers are curved at least about 1, at least about 2, at least about 3, at least about 4, at least about 5, at least about 6, at least about 7, at least about 8, at least about 9, and at least about 10 degrees to facilitate placement in an upper or lower extremity. In some embodiments, one or both chambers have a visible amount of curvature. It is noted that some larger implantation sites, such as the abdomen and the chest, may requires a lesser amount of or even no chamber curvature.

FIG. 6 illustrates the AVG 10 implanted in the upper extremity of a subject. For example, in the illustrated embodiment, the chamber 30 may be connected via conduit 12 to the ulnar artery and the chamber 40 may be connected via conduit 22 to the brachial vein, although multiple, various configurations are contemplated. It can be seen that the chambers 30, 40 may be advantageously curved in such implantation sites to accommodate the puncture-proof or puncture resistant chambers and/or to reduce bending or kinking of the conduits. Also, at least the conduit 52 may be non-kinking or kink-resistant, as described in more detail above.

Referring back to FIG. 4, an outer thin veneer layer 150 may surround and extend along the entire length or substantially the entire length of the graft. In some embodiments, the outer veneer 150 may extend along the entire length of the chambers 30, 40 and the conduit 52 and at least a portion of the length of the conduits 12, 22. The veneer 150 may be formed of biocompatible material (e.g., ePTFE) and may aid in tissue incorporation, hemostasis, and device stability as well as to reduce the likelihood of infection. The veneer may assist in keeping the self-sealing material 80 (or self-sealing layers 90, 110 shown in FIGS. 7 and 8) in place.

As illustrated in FIG. 11, the chambers 30, 40 and/or the veneer layer 150 may include indicia 152 at or adjacent the cannulation ports 30p, 40p to help ensure that the ports 30p, 40p are facing in an upward direction during and after tunneling. For example, the indicia 152 may reside on the veneer 150 above and/or adjacent the ports 30p, 40p and may read "PORT SIDE UP" or the like. Moreover, the conduits 12, 22, 52 and/or the veneer 150 may include indicia to help ensure that the conduits are not twisted during and after tunneling. For example, the indicia 152 may comprise one or more lines on the conduits and/or on the veneer 150 that run along the conduits. The line(s) may further run above or substantially above the center of the port, or may simply indicate the outline of the cannulation area of the cannulation ports 30p, 40p to help ensure that the ports are upward-facing.

Returning to FIG. 4, the chamber housings 30h, 40b may include ledges 82 that extend in the direction of the longitudinal passageways 36, 46 (FIG. 1), and the self-sealing material 80 may be at least partially supported by the ledges 82.

In other embodiments, and as illustrated in FIG. 7, a member 90 comprising a layer of self-sealing material may surround at least a portion of the outer perimeter of the chamber housings 30h, 40h. The member 90 may extend along the entire length or along at least a major portion of the length of the chamber housings 30h, 40h. The members 90 are sized such that self-sealing material covers or extends across the open anterior portion of the chamber housing 30h, 40h and the entire length and width of the ports 30p, 40p.

Figure 8A:
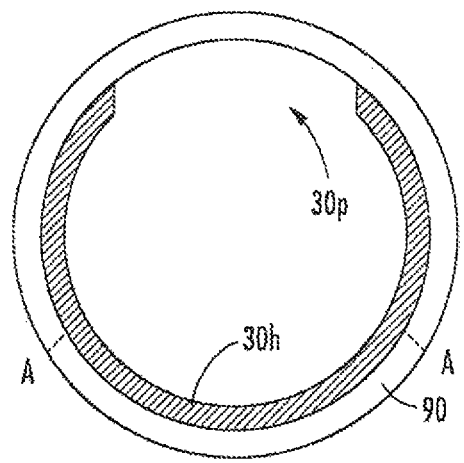
FIGS. 8A-8C illustrate cross-section views of one of the cannulation chambers of FIG. 7 according to various embodiments.
Figure 8B:
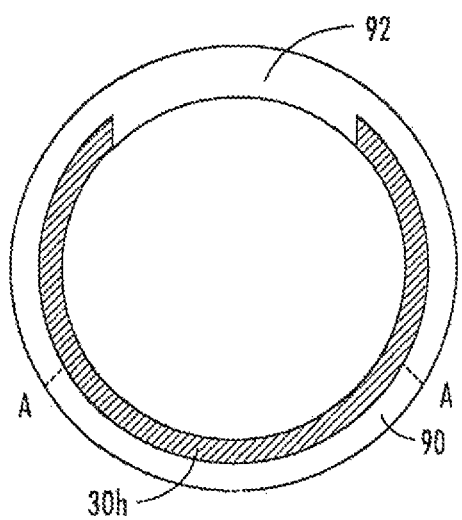
Figure 8C:
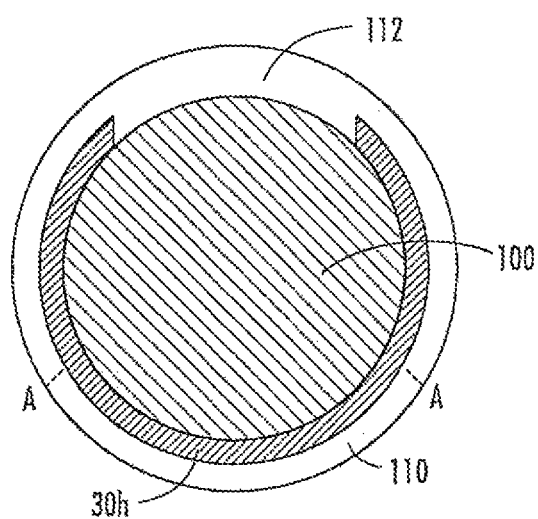

As exemplified in FIGS. 8A-8C, the self sealing material may be positioned relative to the cannulation chamber housing in a variety of ways. FIGS. 8A-8C illustrate a cross-section of the chamber 30. In FIG. 8A, a layer of self-sealing material surrounds at least a portion of the outer perimeter of the chamber housing 30h. The layer of self-sealing material may take the form of the member 90, similar to that shown in FIG. 7. In this regard, the self-sealing material resides over the cannulation port 30p.

Referring to FIG. 8B, the self-sealing material may be as described above with respect to FIG. 8A, but may also include a relatively thicker portion 92 that extends into the cannulation port 30p. This configuration may allow for a longitudinal passageway or flow path that has a circular or substantially circular cross-section so as to minimize disturbance of laminar flow therethrough.

In some embodiments, the member 90 need not surround the entire outer perimeter of the chamber 90; for example, the member may extend to intermediate points adjacent the side walls and/or the posterior wall of the chamber housing 30h (for example, see the points A in FIGS. 8A-8C). In this regard, the member 90 may resiliently fit around a portion or a major portion of the outer perimeter of the chamber housing 30h; this may allow the member 90 to be more easily fitted to and removed from the chamber (e.g., for replacement of member 90).

A layer of self-sealing material may also be formed over the chamber housing 30h. Referring to FIG. 8C, the chamber 30 may be positioned on a template, support fixture, rod, mandrel or the like (shown at 100 and referred to herein as a mandrel). A layer of self-sealing material 110 can then be applied. For example, the chamber housing 30h and mandrel 100 may be fitted in a mold and liquid silicone rubber (or other self-sealing material) may be pumped therein or the mold may be immersed in a liquid bath. Other manufacturing methods known to those of skill in the art for applying the layer of self-sealing material 110 may also be employed.

The mandrel 100 may be sized and configured to define the longitudinal passageway 36 (FIG. 1) through the chamber 30. In some embodiments, the mandrel can be circular or substantially circular in cross-section so as to define a similarly shaped flow path to minimize disturbance of laminar flow. Thus, the layer 110 of self-sealing material may include a relatively thicker portion 112 that extends into the cannulation port 30p.

It is noted that a mandrel or the like may be used in connection with the embodiment shown in FIG. 4. That is, the mandrel may fit beneath the ledges 82 and may be sized and configured to allow a portion 80' of the self-sealing material 80 to extend into the cannulation port 30p. This may allow for the definition of a circular or substantially circular cross-sectional flow path.

Figure 9A:
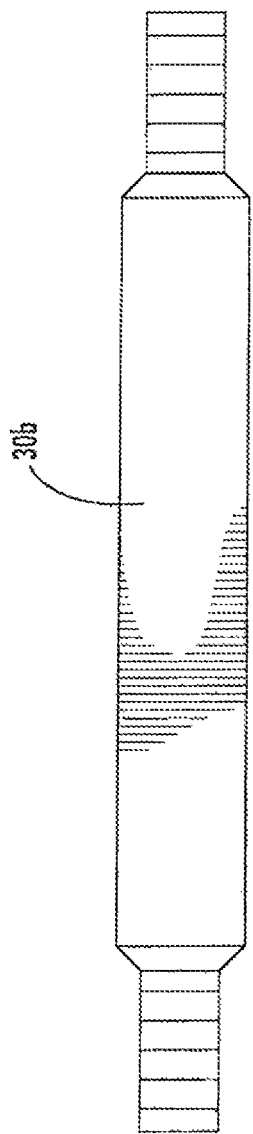
FIG. 9A is bottom view of a cannulation chamber for use with the AVG of FIG. 1 according to some embodiments.
Figure 9B:
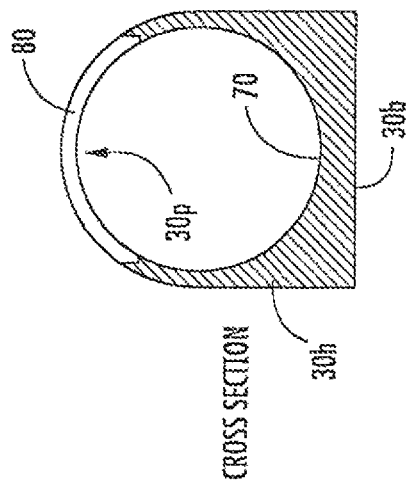
FIG. 9B is a cross-sectional view of the cannulation chamber of FIG. 9A according to some embodiments.

In some embodiments, the chambers/chamber housings may have a squared or flat bottom portion. For example, as illustrated in FIGS. 9A and 9B, the chamber housing 30h may have a flat or squared bottom portion 30b adjacent the posterior wall 70 to help prevent the chamber from rolling or twisting as it is being tunneled through tissue. In this regard, the squared or flat bottom portion 30b may assist in maintaining the cannulation ports 30p in an upward-facing configuration both during and after tunneling.

Figure 10A:
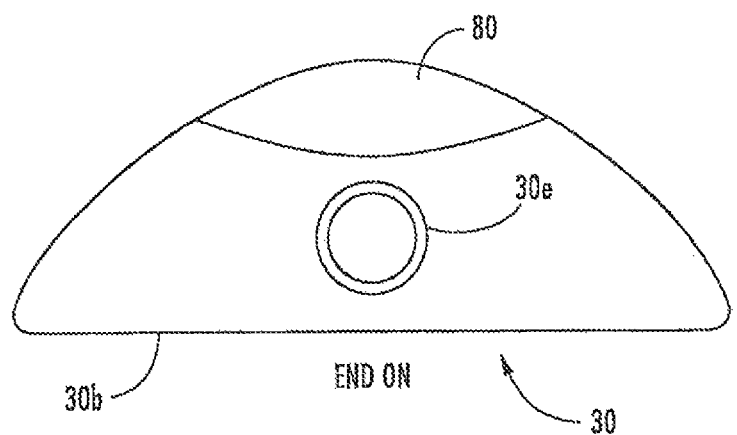
FIG. 10A is an end view of a cannulation chamber for use with the AVG of FIG. 1 according to some embodiments.
Figure 10B:
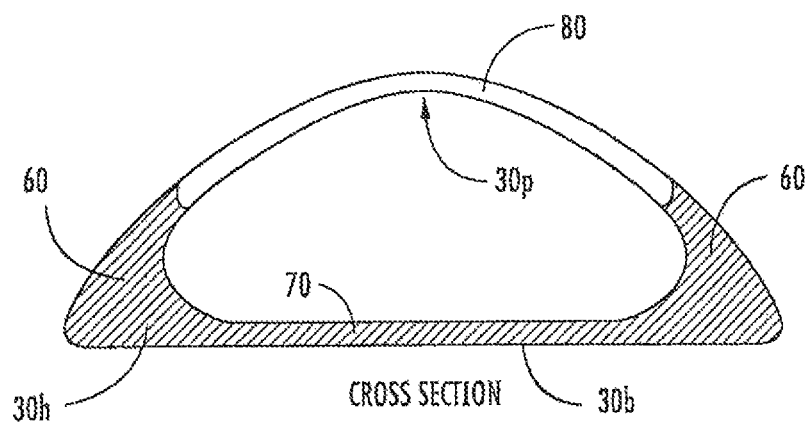
FIG. 10B is a cross-sectional view of the cannulation chamber of FIG. 10A according to some embodiments.

In other embodiments, the chambers/chamber housings may also have a domed or generally triangular shape when viewed from the end or cross-section. For example, as illustrated in FIGS. 10A and 10B, at least a portion of sidewalls 60 of the chamber housing 30h may extend inwardly from the bottom portions 30b, 40b toward the open anterior portion of the chamber housing 30h adjacent the port 30p.

An AVG 200 according to other embodiments is illustrated in FIGS. 11-13. The AVG 200 may include any of the features described above in reference to the AVG 10. The primary difference in the embodiment shown in FIGS. 11-13 is a reduction in the number of fluid (e.g., blood) contacting components. That is, in the earlier described embodiments, the fluid may contact a plurality of components, including the conduits 12, 22, 52, the chamber housings 30h, 40h and/or the self-sealing material 80 associated with the housings 30h, 40h. In the embodiment shown in FIGS. 10-12, one or more conduits may extend through the chambers 30, 40 to thereby reduce the number of fluid contacting surfaces.

The AVG 200 includes at least one conduit 202 having first and second end portions 12', 22'. The first end portion 12' is configured to connect to an artery of a subject at a first end 14' and the second end portion is configured to connect to a vein of the subject at a first end 24'. In this regard, blood flows through the conduit 202 from the first end portion 12' to the second end portion 22'. Although not shown, at least a portion of the conduit 202 may be non-kinking or kink-resistant. For example, at least a portion of a middle portion 52' of the conduit 202 residing between the chambers 30, 40 may be beaded, as described above.

As illustrated, a pair of cannulation chambers 30, 40 are positioned between the first and second end portions 12', 22' of the conduit 202. The chambers 30, 40 are as described above. With reference to FIG. 12, the chamber 40 includes an elongated housing 40h having an inlet 42 and an outlet 44, a pair of side walls 60, a posterior wall 70, and an open anterior portion including an aperture defining the cannulation port 40p. Self-sealing material 80 extends across the open anterior portion of the housing 40h (i.e., across the port 40p). A longitudinal passageway 46 is defined by the housing 40h and the self-sealing material 80. The at least one conduit 202 extends through the passageway 46 and therefore defines a longitudinal fluid passageway 46' through the at least one conduit 202. The self-sealing material 80 and the conduit 202 may be adhered via a medical-grade adhesive 206. This configuration may prevent the two components from separating as a needle is inserted therethrough. The medical-grade adhesive 206 may also adhere the conduit 202 to the chamber housing 40h.

The chamber 30 may have a similar or identical configuration. The portion of the AVG 200 including the chamber 30 is shown as including the outer veneer 150, although it will be understood that the outer veneer 150 will typically extend over at least a portion of the AVG 200 including the chamber 40.

Figure 14:
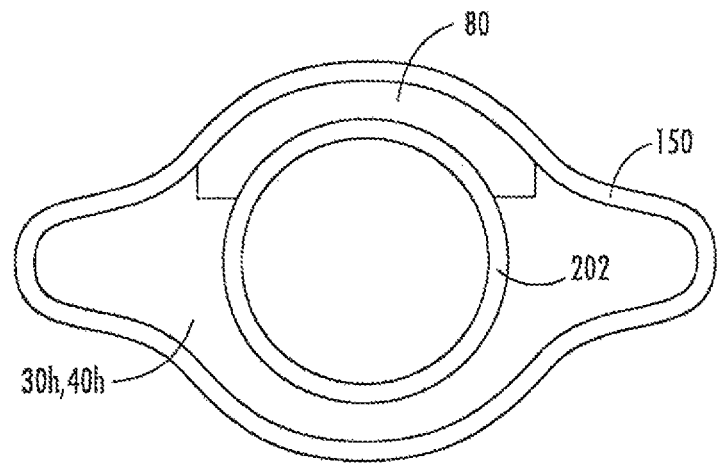
FIGS. 14 and 15 illustrate cross-sectional views of cannulation chambers of the AVG of FIG. 11 according to some other embodiments.
Figure 15:
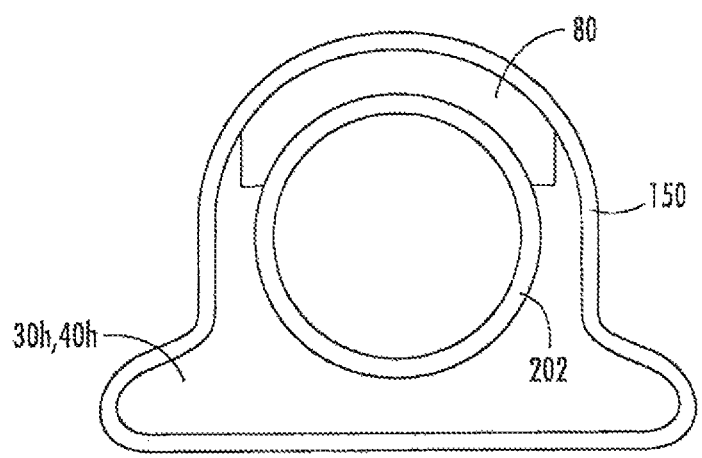

Alternative chamber cross-section views are shown in FIGS. 14 and 15. Although the conduit 202 is shown extending through the chamber housings 30h, 40h, it will be appreciated that these chamber designs may be used with the AVG 10 described above. The chamber housings 30h, 40h shown in FIGS. 14 and 15 are elongated along a center or a bottom portion of the housing, and may thereby assist in maintaining the cannulation ports in an upward-facing configuration both during and after tunneling in much the same way as the configurations illustrated in FIGS. 9 and 10.

Figure 16:
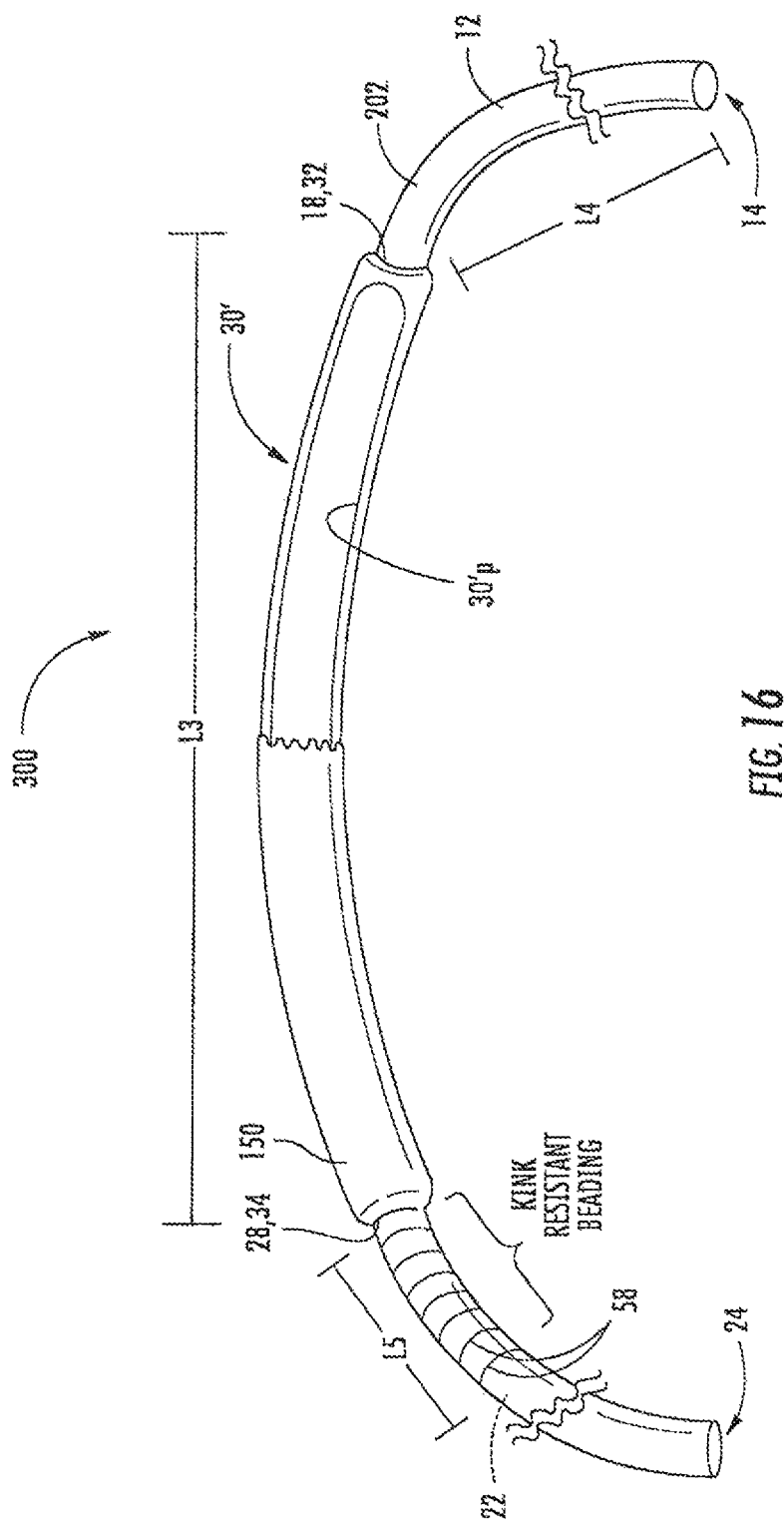
FIG. 16 is a schematic illustration of an AVG according to some other embodiments.

An AVG 300 according to other embodiments is illustrated in FIG. 16. The primary difference in this embodiment is that the AVG 300 includes only one cannulation chamber 30'. The AVG 300 may include a conduit 202 extending through the housing of the chamber 30' in much the same way as described above in connection with the AVG 200. Alternatively, the AVG 300 may include first and second conduits 12, 22 in much the same way as described above in connection with the AVG 10. That is, the first conduit 12 connects an artery and the chamber inlet 32 and the second conduit 22 connects the chamber outlet 34 and a vein.

The chamber 30' may have a length greater than above-described lengths for the chambers 30, 40 so as to provide an increased surface area for the cannulation port 30'p. In various embodiments, the length L3 may be between about 10 cm and about 20 cm and between about 10 cm and about 15 cm. The chamber 30' may have increased curvature due to the lack of a second curved chamber and/or a middle conduit portion. According to various embodiments, the chamber 30' may have an arc or a curve angle (see FIG. 5) of between about 5 and about 90 degrees, between about 15 and about 90 degrees, between about 30 and about 80 degrees, and greater than about 40 degrees to accommodate placement in, for example, an upper arm of a subject. The conduits 12, 14 (or equivalent portions of the conduit 202) may have a length L4 of between about 10 cm and about 20 cm and may also be trimmed to suit a particular application. At a portion of at least one of the conduits 12, 14 (or equivalent portions of the conduit 202) may be kink-proof or kink-resistant. As illustrated, beading material 58 is wrapped around a length L5 of the conduit 22 adjacent the chamber 30'.

Figure 17:
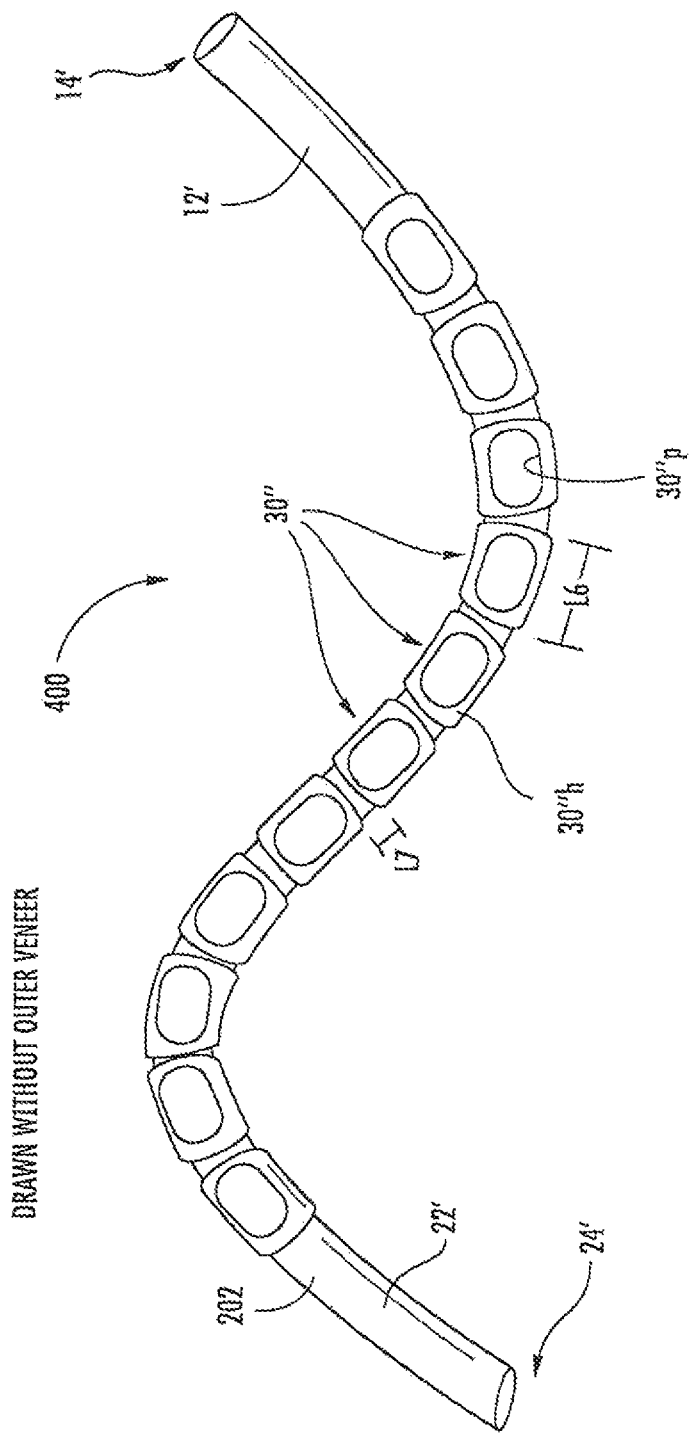
FIG. 17 is a schematic illustration of an AVG according to some other embodiments.

An AVG 400 according to other embodiments is shown in FIG. 17. The primary difference in this embodiment is that the AVG 400 includes three or more cannulation chambers 30". As illustrated, the AVG 400 includes 11 chambers 30"; however, it will be appreciated that fewer or more chambers may be employed. Each chamber 30" may include all the features described above in connection with the chambers 30, 40 and 30'. That is, each chamber 30" includes a housing 30"h having an inlet, an outlet and an open anterior portion defining a cannulation port 30"p with self-sealing material extending across or adjacent the cannulation port. Thus, each chamber 30" has a longitudinal passageway therethrough as described above.

Each chamber 30" will generally have a shorter length L6 than as described above in the other embodiments. The length L6 may be between about 1 cm and about 7 cm, between about 1 cm and about 5 cm, and about 3 cm in various embodiments.

The AVG 400 may include a conduit 202 extending through the longitudinal passageway each chamber 30" in much the same way as described above in connection with the AVG 200. The chambers 30" will generally be spaced closer together than in the embodiments described above. The length L7 of the spacing may be between about 0.25 cm and about 5 cm, between about 0.25 cm and about 2 cm, and between about 0.5 cm and about 1 cm in various embodiments.

The AVG 400 may provide flexibility when being implanted in a subject. That is, the AVG 400 may be bent or otherwise manipulated to accommodate a particular implantation site. Also, the plurality of chambers have an generally large overall surface area of self-sealing material, thereby retaining the advantages described above.

Figure 18:
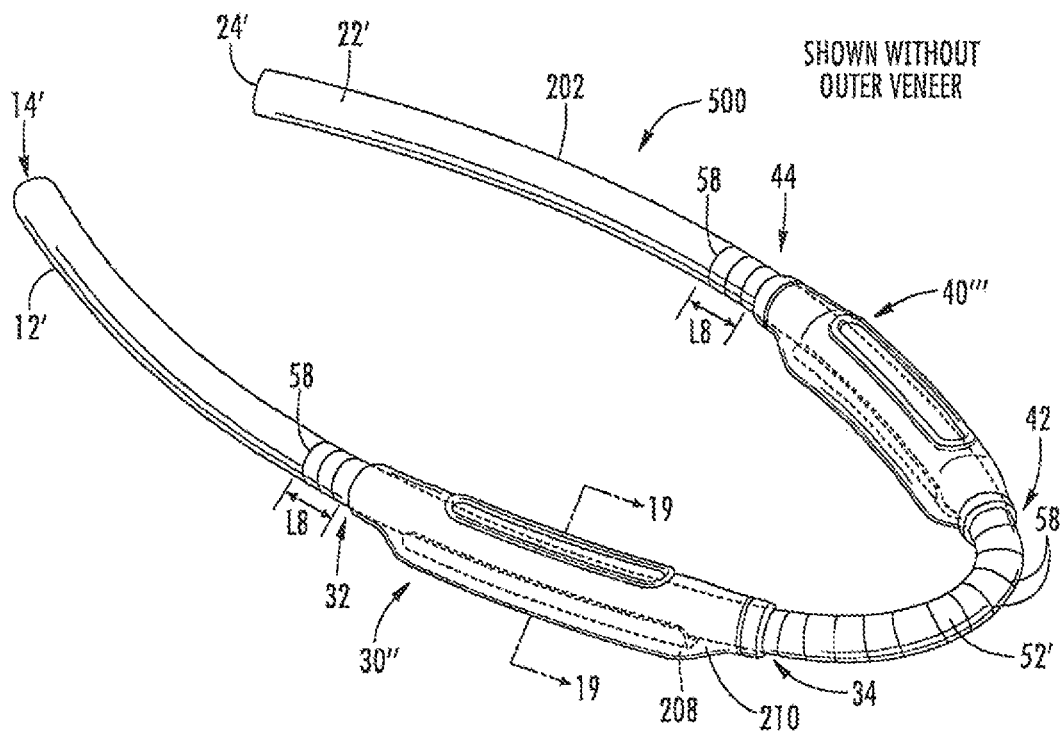
FIG. 18 is a schematic illustration of an AVG according to some other embodiments.

An AVG 500 according to other embodiments is illustrated in FIG. 18. The AVG 500 may include features described above in reference to the AVGs 10, 200 and 300. Like the AVG 200 shown in FIGS. 11-13, the AVG 500 may have a reduced number of fluid (e.g., blood) contacting components. The chambers of the AVG 500 are constructed somewhat differently than the chambers of the AVGs 10, 200 and 300, as will be described below.

The AVG 500 includes a conduit 202 having first and second end portions 12', 22'. The conduit 202 may be formed of an inert biocompatible material such as ePTFE, polyurethane, Dacron, or the like. The first end portion 12' is configured to connect to an artery of a subject at an end 14' thereof, like the end 14 shown in FIG. 1. The second end portion 22' is configured to connect to a vein of the subject at an end 24' thereof, much like the end 24 shown in FIG. 1. In this regard, blood flows through the conduit 202 from the first end portion 12' to the second end portion 22'.

As illustrated, a pair of cannulation chambers 30''', 40''' are positioned in a spaced-apart relationship between the first and second end portions 12', 22' of the conduit 202. The chambers 30''', 40''' may be identical or substantially identical. The chamber 30''' includes an inlet 32 and an outlet 34. The chamber 40''' includes an inlet 42 and an outlet 44. The conduit 202 extends through the chamber 30''' from the inlet 32 to the outlet 34. The conduit 202 extends through the chamber 40''' from the inlet 42 to the outlet 44. A middle portion 52' of the conduit 202 is disposed between the chambers 30''', 40'''.

Each of the chambers 30''', 40''' includes an elongated chamber body 210 that surrounds the conduit 202. The chamber bodies 210 define the respective chamber inlets 32, 42 and the chamber outlets 34, 44. Each of the chambers 30''', 40''' also includes an elongated shell or shield 208. The shell 208 may be embedded in the chamber body 210.

Figure 19:
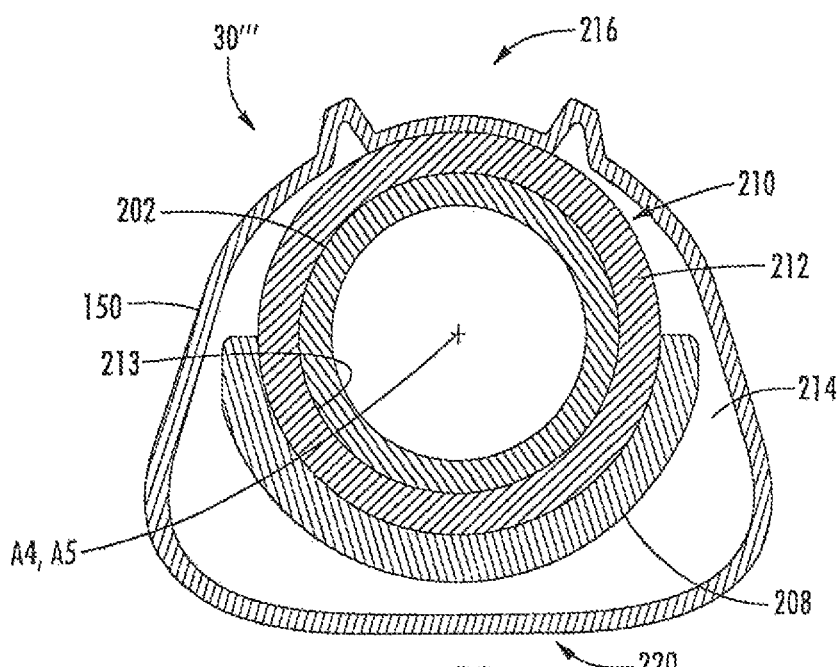
FIG. 19 is a cross-sectional view of a cannulation chamber of the AVG of FIG. 18 according to some other embodiments.

A cross sectional view of the chamber 30''' is shown in FIG. 19. As illustrated, the chamber body 210 includes an inner layer 212 and an outer layer 214. The inner layer 212 may be annular and define a chamber passageway 213. The chamber passageway 213 may have a longitudinal axis A4 that corresponds to a longitudinal axis A5 of the conduit 202 (e.g., a fluid flow passageway or path of the conduit 202). The shell 208 may be disposed between the inner layer 212 and the outer layer 214.

Figure 20:
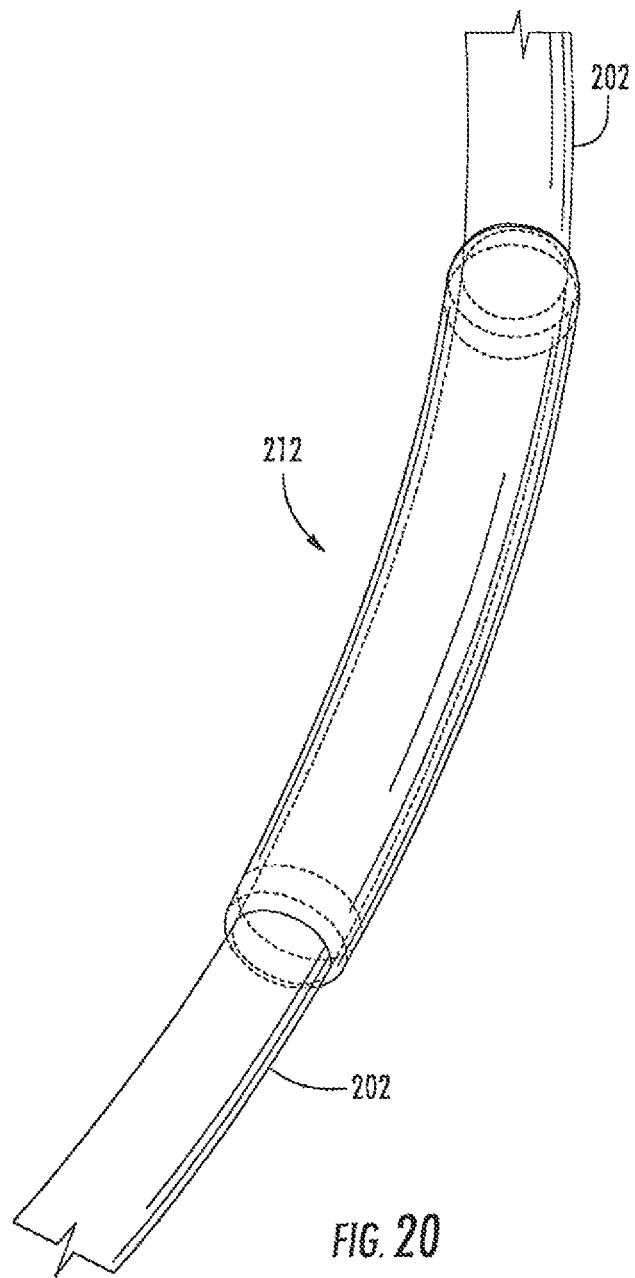
FIG. 20 is a perspective view of an inner layer of the cannulation chamber of FIG. 19 according to some embodiments.

Referring to FIGS. 19 and 20, the inner layer 212 may fit over the conduit 202. The inner layer 212 may be molded around the conduit 202. The inner layer 212 may be adhered or otherwise attached to the conduit 202. The inner layer 212 is formed of a self-sealing material (e.g., but not limited to, silicone).

Figure 21:
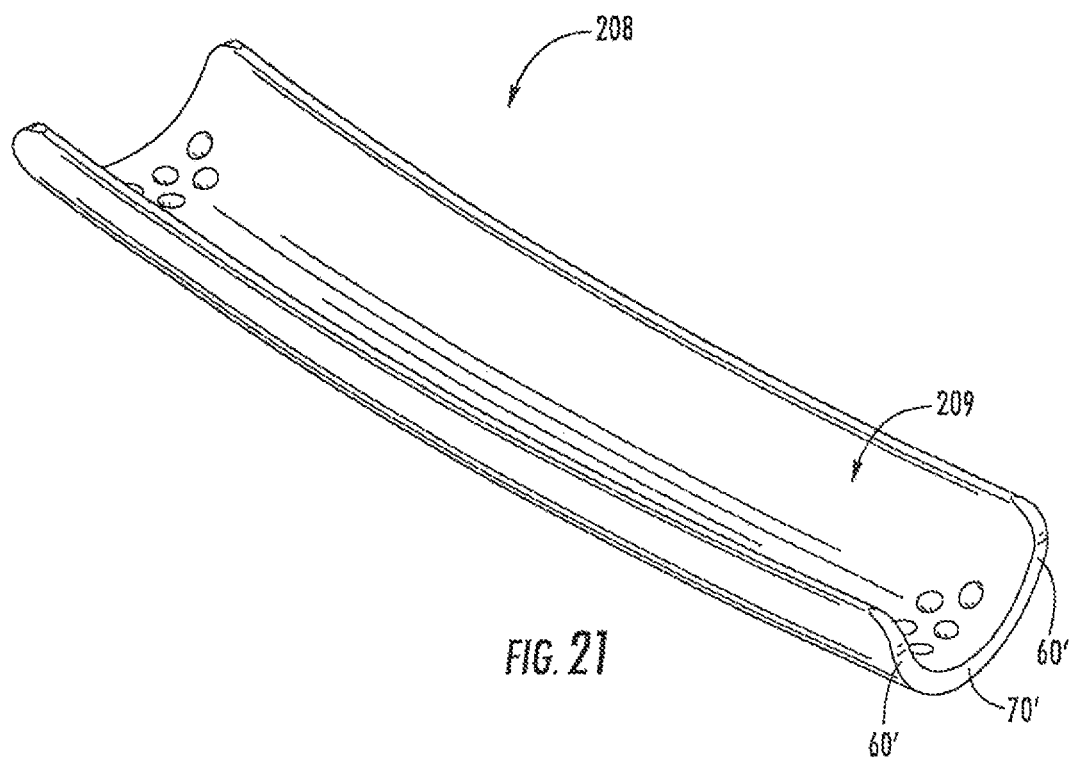
FIG. 21 is a perspective view of a shell of the cannulation chamber of FIG. 19 according to some embodiments.

Turning to FIGS. 19-21, the inner layer 212 may be received in a cavity 209 of the shell 208. The shell 208 may be molded to the inner layer 212. The shell 208 may be adhered or otherwise attached to the inner layer 212. The shell 208 may generally have the shape of an open-ended semi-cylinder and therefore surround about 180 degrees of the outer circumference of the inner layer 212. The shell 208 may be C-shaped or U-shaped. The shell 208 includes a posterior wall 70' and opposing sidewalls 60' defining the cavity 209. The shell 208 has a length that is at least a major portion of the length of the inner layer 212. In some embodiments, the length of the shell 208 and the inner layer 212 are substantially the same. The shell 208 is formed of a substantially rigid biocompatible material (e.g., titanium or a substantially rigid polymer or composite).

Referring to FIGS. 19 and 22, the shell 208 and the inner layer 212 may be received in the outer layer 214. The outer layer 214 may be molded around the inner layer 212 and/or the shell 208. The inner layer 212 and/or the shell 208 may be adhered or otherwise attached to the outer layer 214. The outer layer 214 may be formed of any suitable material; for example, a material that facilitates bonding or molding with the inner layer 212. The outer layer may be formed of a self-sealing material (e.g., but not limited to, silicone).

The outer layer 214 includes a cannulation port 216. In place, the cannulation port 216 exposes the self-sealing material of the inner layer 212. In some embodiments, the outer layer 214 can include an additional layer of self-sealing material across the cannulation port 216.

The chamber body 210 may include cannulation port locating features. For example, the cannulation port 216 may include a raised perimeter or perimeter portion 218 such that the cannulation port can be tactilely and/or visually identified when the AVG 500 is implanted in a subject. That is, the raised perimeter 218 may be visible through the skin of the subject and/or felt through the skin by medical personnel.

It will be understood that, like the other embodiments described above, when a dialysis needle is inserted through the cannulation port 216 and the self-sealing material (e.g., the inner layer 212), the needle may be inhibited or prevented from extending through the shell 208 (e.g., the posterior or the side walls of the shell 208).

It will be appreciated that the shell 208, the inner layer 212 and the outer layer 214 of the chamber housing 210 may be provided as an integrated chamber 30''' rather than assembled as described above. The chamber 30''' may then be fit onto a graft conduit, such as the conduit 202. For example, the conduit 202 may be received in the chamber passageway 213 (e.g., pulled through the chamber passageway 213). The chamber 30''' may also be molded to the conduit 202 or otherwise attached (e.g., adhered) to the conduit 202.

Turning again to FIG. 18, beading material 58 may be included on the outer periphery of the middle portion 52' of the conduit 202. Also, as illustrated, beading material 58 may be wrapped around a length L6 of the conduit 202 adjacent the chamber 30''' and/or the chamber 40'''. In some embodiments, the length L6 is about 1 to 2 cm.

As illustrated in FIG. 19, the outer veneer 150 may be provided over at least a portion of the AVG 500. Although not shown in FIG. 18, it will be understood that the outer veneer 150 will typically extend over at least a major portion of the AVG 500 including the chambers 30''' and 40''' and the middle portion 52' of the conduit 202. The outer veneer 150 may also extend from the chambers 30''', 40''' toward or to the first and second end portion 12', 24' of the conduit 202.

The chambers 30''', 40''' may include a flattened bottom portion or surface 220. As described above, such a configuration may inhibit malpositioning and/or twisting of the graft. The chambers/chamber bodies may have a domed or generally triangular shape when viewed from the end or cross-section. In some other embodiments, the chambers/chamber bodies may have a substantially circular cross-section, an elliptical cross-section or a generally oval cross-section.

Turning to FIG. 23, the chambers 30''', 40''' may be curved to have are angles A1, A2 in the same manner as described above in connection with the chamber 30. The arc angles A1 and A2 may be equal for a particular chamber 30'''. The values of the arc angles A1, A2 may be as described above in connection with the chamber 30. For example, the angles A1 and A2 may be between about 10 and 30 degrees to facilitate placement in an upper extremity of a patient.

The chambers 30''' and 40''' each have a center portion or section and opposed end portions or sections (e.g., the center portion 30c and the end portions 30e shown in FIG. 23). The chambers 30''' and 40''' may have the same dimensions as the dimensions of the chambers 30, 40 described above. The cannulation ports 216 may have the same dimensions as the dimensions of the cannulation ports 30p, 40p described above. The conduit 202, including the first end portion 12', the second end portion 22' and the middle portion 52', may have the same dimensions and properties as the conduits 12, 22 and 52 described above.

It is contemplated that the chambers described herein may be supplied separately from their associate conduit(s). For example, the chamber 30''' and/or the chamber 40''' may be provided to a clinician, who may then fit the chambers 30''' and/or 40''' to an off-the shelf graft conduit as needed for a particular application.

It is also contemplated that various components described above may be supplied as a medical kit. For example, the chambers 30''' and/or 40''' (or the components thereof) may be supplied with the conduit 202 for later assembly and use.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention.

That which is claimed is:

1. An arteriovenous dialysis graft, comprising:
a flexible conduit; and
a cannulation chamber including:
an elongated outer chamber body having an annular chamber passageway adapted to receive and surround a portion of the conduit, the chamber body comprising self-sealing material and a cannulation port that exposes the self-sealing material; and
an elongated shell embedded in the chamber body and extending generally parallel to and partially surrounding the chamber passageway, the shell including a posterior wall, a pair of sidewalls, and an open anterior portion facing the cannulation port of the chamber body,
wherein the chamber body includes an inner layer and an outer layer, the inner layer adapted to be molded around the conduit and the outer layer adapted to be molded to the inner layer with the shell therebetween.

2. An arteriovenous dialysis access graft configured to be implanted in a subject between a first blood vessel and a second blood vessel of the subject, the arteriovenous graft comprising:
a flexible conduit defining a longitudinal flow passageway such that blood flows through the longitudinal flow passageway of the conduit from the first blood vessel to the second blood vessel; and
a cannulation chamber including:
an elongated chamber body defining an opening configured to receive and surround a portion of the conduit, the chamber body comprising:
an annular inner layer including self-sealing material surrounding the conduit, and an outer layer around the inner layer and defining a cannulation port that exposes the self-sealing material; and
an elongated shell embedded in the chamber body between the inner layer of the chamber body and the outer layer of the chamber body and extending generally parallel to the longitudinal flow passageway of the conduit, the shell including:
a posterior wall; and
a pair of sidewalls defining an open anterior portion facing the cannulation port of the chamber body,
wherein the shell is formed of a substantially rigid material such that, when a dialysis needle is inserted through the cannulation port and the self-sealing material, the needle is inhibited or prevented from extending through the posterior wall or the sidewalls of the shell.

3. The arteriovenous dialysis graft of claim 2, wherein the outer layer of the chamber body adjacent to the cannulation port includes a raised perimeter portion such that the cannulation port can be tactilely and/or visually identified.

4. The arteriovenous dialysis graft of claim 2, wherein each chamber is curved to have an arc angle formed by a longitudinal axis at one end of the curved chamber and an axis parallel to a longitudinal axis of a straight chamber that is between 10 and 30 degrees to accommodate placement in an arm of a subject.

5. The arteriovenous dialysis graft of claim 2, wherein each chamber body has a flattened bottom to inhibit malpositioning and/or twisting of the graft.

6. An arteriovenous dialysis access graft configured to be implanted in a subject between a first blood vessel and a second blood vessel of the subject, the arteriovenous graft comprising:
a flexible conduit defining a longitudinal flow passageway between the first blood vessel and the second blood vessel such that blood flows through the longitudinal flow passageway of the conduit from the first blood vessel to the second blood vessel; and
a cannulation chamber including an elongated chamber body defining an opening adapted to receive and surround a portion of the conduit, the chamber body comprising:
self-sealing material;
a cannulation port that exposes the self-sealing material; and
an elongated shell embedded in the self-sealing material of the chamber body and extending generally parallel to the longitudinal flow passageway of the conduit, the shell including:
a posterior wall; and
a pair of sidewalls defining an open anterior portion facing the cannulation port of the chamber body,
wherein the self-sealing material surrounds each of the conduit and the shell and is received in the open anterior portion of the shell,
and wherein the shell is formed of a substantially rigid material such that, when a dialysis needle is inserted through the cannulation port and the self-sealing material, the needle is inhibited or prevented from extending through the posterior wall or the sidewalls of the shell.

7. The arteriovenous dialysis graft of claim 6, wherein the cannulation port includes a raised perimeter portion such that the cannulation port can be tactilely and/or visually identified.

8. The arteriovenous dialysis graft of claim 6, wherein the chamber is curved to have an arc angle that is between 10 and 30 degrees to accommodate placement in an arm of a subject.

9. The arteriovenous dialysis graft of claim 6, wherein the chamber body has a flattened bottom to inhibit repositioning and/or twisting of the graft.

* * * * *